(12) United States Patent
Kuo

(10) Patent No.: US 12,297,492 B2
(45) Date of Patent: May 13, 2025

(54) AMPLIFICATION OF SINGLE STRANDED DNA

(71) Applicant: WOBBLE GENOMICS LIMITED, Edinburgh (GB)

(72) Inventor: Richard Izen Kuo, Lothian (GB)

(73) Assignee: Wobble Genomics Limited, Edinburgh (GB)

( * ) Notice: Subject to any disclaimer, the term of this patent is extended or adjusted under 35 U.S.C. 154(b) by 0 days.

(21) Appl. No.: 18/288,370

(22) PCT Filed: Apr. 26, 2022

(86) PCT No.: PCT/EP2022/060961
§ 371 (c)(1),
(2) Date: Oct. 25, 2023

(87) PCT Pub. No.: WO2022/229128
PCT Pub. Date: Nov. 3, 2022

(65) Prior Publication Data
US 2024/0263224 A1    Aug. 8, 2024

(30) Foreign Application Priority Data
Apr. 26, 2021 (GB) .................................. 2105947

(51) Int. Cl.
*C12Q 1/6865* (2018.01)
*C12Q 1/6806* (2018.01)
*C12Q 1/6855* (2018.01)

(52) U.S. Cl.
CPC ......... *C12Q 1/6855* (2013.01); *C12Q 1/6806* (2013.01)

(58) Field of Classification Search
CPC ........................... C12Q 1/6806; C12Q 1/6855
See application file for complete search history.

(56) References Cited

U.S. PATENT DOCUMENTS

2019/0264201 A1    8/2019    Pugh et al.

OTHER PUBLICATIONS

Kuo, R et al. Normalized long read RNA sequencing in chicken reveals transcriptome complexity similar to human. 2017. BMC Genomics, 18:323. 1-19. (Year: 2017).*
International Preliminary Report on Patentability, Nov. 24, 2023, Appln. No. PCT/EP2022/060961, 19 pages.
Written Opinion of the International Preliminary Examining Authority, Feb. 17, 2023, Appln. No. PCT/EP2022/060961, 8 pages.
Written Opinion of the International Searching Authority, Aug. 19, 2022, Appln. No. PCT/EP2022/060961, 7 pages.

(Continued)

*Primary Examiner* — Samuel C Woolwine
*Assistant Examiner* — Lisa Horth
(74) *Attorney, Agent, or Firm* — Brian E. Davy; Bozicevic, Field & Francis LLP

(57) ABSTRACT

The present invention relates to methods, kits and compositions for selective amplification of single stranded DNA. The invention is useful in generating a normalized cDNA fraction and it can be used in various RNA and DNA sequencing applications to amplify DNA templates having pre-attached adapters. We describe a method of selective amplification of single stranded cDNA. We also describe an oligonucleotide dimer composition for use in a method and a selective amplification kit for selectively amplifying low abundance cDNA from a cDNA sample.

19 Claims, 8 Drawing Sheets

Specification includes a Sequence Listing.

Addition of lig sequences to the ends of single stranded cDNA templates.

(56) References Cited

OTHER PUBLICATIONS

Shcheglov et al. (2007) "Normalization of cDNA libraries" Nucleic Acids Hybridization, 97-124.
Zhulidov et al. (2004) "Simple cDNA normalization using kamchatka crab duplex-specific nuclease" Nucleic Acids Research, 32(3):1-8.

* cited by examiner

Overview of Level-Up normalization process.

Front and Back K-linker structures as shown annealed to single strand cDNA template.

Length distribution from gel electrophoresis of input cDNA.

Length distribution from gel electrophoresis of normalized cDNA.

Saturation curves for input cDNA and Level-Up normalized cDNA using Nanopore cDNA sequencing.

AMPLIFICATION OF SINGLE STRANDED DNA

FIELD OF INVENTION

The present invention relates to methods, kits and compositions for selective amplification of single stranded DNA. The invention is useful in generating a normalized cDNA fraction and it can be used in various RNA and DNA sequencing applications to amplify DNA templates having pre-attached adapters.

INCORPORATION BY REFERENCE OF SEQUENCE LISTING PROVIDED AS A TEXT FILE

A Sequence Listing is provided herewith in a text file, BOULT-053_SEQ_LIST_ST25, created on Mar. 28, 2024 and having a size of 1,833 bytes. The contents of the text file are incorporated herein by reference in its entirety.

BACKGROUND

RNA sequencing has become a powerful tool for understanding biology (Stark, R., Grzelak, M. & Hadfield, J. RNA sequencing: the teenage years. Nat. Rev. Genet. 20, 631-656 (2019)). Its applications range from drug development to improving agriculture. RNA sequencing is typically used for identifying differences between biological samples. These could be samples from infected and control animals to study disease resistance or samples from the same sample type over a time course to understand growth and development. The primary results generated from RNA sequencing are the discovery of all genes and isoforms that are expressed in a sample and the quantification of expression. Most cells and tissues share many of the same highly expressed genes which are commonly known as house-keeping genes. These genes are typically responsible for basic cell functions and thus do not provide cell specific characteristics. Since these house-keeping genes typically make up a large fraction of RNA within a sample, RNA sequencing data is usually dominated by sequencing reads from these non-informative RNA. This phenomenon results in two main negative effects on generating good results from RNA sequencing projects; first, genes and isoforms which are specific to the condition in question are difficult to detect, and second, the data generated is, in large part, redundant.

The first main negative effect has two consequences. The first is that the amount of sequencing required to detect genes of interest must be large enough to handle sampling inefficiencies caused by the low relative abundance of genes of interest. The second being that, in some cases, low abundance target genes may be simply impractical to identify. This can be evidenced by the still ongoing efforts to annotate the human genome where even after thousands of sequencing projects the full human transcriptome is still elusive with novel isoforms and genes being reported with regularity. Since eukaryotic transcriptomes derive their complexity from alternative splicing which generates combinatorial permutations, the search for novel RNA will likely be a constant endeavour.

These two consequences ultimately hamper scientific progress by limiting the abilities of researchers to produce ideal results from their sequencing experiments. These consequences also contribute to the impracticality of applying RNA sequencing toward a wider range of uses. For instance, for use in diagnostics and treatment tracking where the volume of sequencing required would be both time and cost prohibitive.

The second main negative effect (generation of redundant data) also has two main consequences. The first is that more data requires more processing time which increases overall cost and time of RNA sequencing experiments. These costs are both in terms of energy from additional computation required and work time from bioinformaticians that are tasked with processing the data. The second consequence is that redundant data results in the need for more storage. As sequencing is becoming more widespread, data storage has become a significant problem. For RNA sequencing technology to take on more roles, more efficient data generation is necessary to reduce storage requirements.

To address issues with high abundance house-keeping genes reducing sampling efficiency for genes of interest, complementary DNA (cDNA) normalization was developed (Alex S. Shcheglov, Pavel A. Zhulidov, Ekaterina A. Bogdanova, D. A. S. Normalization of cDNA Libraries, Nucleic Acids Hybrid. CHAPTER 5, (2014)). Since RNA sequencing typically relies on the conversion of RNA to double stranded cDNA, cDNA normalization takes advantage of the biochemical properties of cDNA to generate a uniform distribution of unique genes and isoforms within a cDNA library. In theory, the maximum non-targeted sampling efficiency is produced if all unique RNA sequences are represented at the same relative abundance. Thus the objective of normalization is to re-distribute a cDNA library to meet this criterion as closely as possible.

There are two forms of full length cDNA normalization that have been previously developed: the Duplex Specific Nuclease (DSN) method (Zhulidov, P. A. et al. Simple cDNA normalization using kamchatka crab duplex-specific nuclease. Nucleic Acids Res. 32, e37 (2004)) and the hydroxyapatite column method (Andrews-Pfannkoch, C., Fadrosh, D. W., Thorpe, J. & Williamson, S. J. Hydroxyapatite-mediated separation of double-stranded DNA, single-stranded DNA, and RNA genomes from natural viral assemblages. Appl. Environ. Microbiol. 76, 5039-5045 (2010)). Both methods rely on the denaturation and re-hybridization of cDNA strands. As the single stranded cDNA move about in solution, the sequences that are more highly abundant have a greater probability of finding a matching complementary sequence with which to re-hybridize. Thus, as re-hybridization reaches its limit, the remaining single stranded cDNA represents a normalized sequence library.

The difference between the two methods lies in their approach for isolating the single stranded cDNA library from the re-hybridized double stranded cDNA molecules.

In the DSN method, an enzyme which specifically cleaves double stranded DNA is used to decompose all double stranded cDNA within the solution. The solution is then purified and size-selected for cDNA sequences above a certain length. These sequences are then amplified using the Polymerase Chain Reaction (PCR).

In the column method, the denatured and re-hybridized cDNA library is passed through a heated column filled with hydroxyapatite granules. The hydroxyapatite preferentially binds to larger DNA molecules. The size of DNA that is bound is controlled by the concentration of phosphate buffer in which the cDNA library is dissolved. Thus the concentration of phosphate buffer must be tuned specifically for cDNA molecules within a certain range of sequence length. The cDNA is eluted through the column using increasing concentrations of phosphate buffer to extract increasing sizes of DNA molecules. Since the single stranded cDNA will be roughly one half the size of the re-hybridized cDNA, elution of the single stranded fraction can be managed if the mean cDNA sequence length is known.

The resulting elution is intended to be enriched for the single stranded cDNA which are then amplified using PCR.

In both the DSN and column methods, known adapters must be attached to the ends of the cDNA prior to normalization to facilitate PCR amplification (so that appropriate primers can be used).

Since both methods are subtractive by nature with the depletion of large fractions of cDNA, the amount of starting cDNA is typically required to be higher than 1 µg for the DSN approach and 4 µg for the column approach.

Since the DSN method uses enzymes which cleave all double stranded cDNA, in theory it can deplete low abundance sequences with segments that match high abundance sequences. This effect can also increase the probability of forming PCR chimeras. PCR chimeras are formed when incomplete single stranded cDNA sequences act as primers to other sequences thus combining the sequences in a way that does not occur in nature. PCR chimeras represent false positives for novel isoforms and are extremely challenging to distinguish from true alternative isoforms. Validating PCR chimeras typically requires in-depth biochemical assays. Both the depletion of low abundance sequences and the increased potential for PCR chimeras make the DSN method unsuitable for many RNA sequencing applications.

Since the column method only allows for segregation of high abundance and low abundance fractions within a narrow size range, it has significant bias against longer cDNA sequences. The effect of this is a loss of representation for longer RNA sequences. This effect makes it unsuitable for many RNA sequencing applications.

Accordingly, it is with these problems in mind that the present invention has been devised.

SUMMARY OF INVENTION

In its broadest aspect, the present invention provides methods, compositions and kits for selective amplification of low abundance cDNA from a cDNA sample. The present invention provides for non-depletion normalisation of a cDNA sample, particularly for normalisation of a cDNA sample by increasing the amount of low abundance cDNA within the cDNA sample. Advantages of the present invention over previous normalisation technologies include:
1. A much smaller amount of starting material required;
2. Reduced risk of over depletion resulting in missing genes;
3. Reduced propensity to create PCR artifacts which could produce false positives for transcript discovery/detection;
4. Template switching oligo (TSO) cleanup (clean-up of cDNA without adaptors) takes place when the methods, compositions and kits are employed.

According to the present invention there is provided a method of selective amplification of single stranded cDNA, the method comprising:
(i) providing a cDNA sample comprising double stranded cDNA templates, each template having a known 5' pre-attached adapter and a known 3' pre-attached adapter;
(ii) denaturing the cDNA sample to produce single stranded cDNA templates;
(iii) re-associating the cDNA sample to produce a mixture of post-association single stranded cDNA templates and post-association double stranded cDNA templates;
(iv) annealing a 5' adapter complex to the 5' pre-attached adapter of at least one post-association single stranded cDNA template, and annealing a 3' adapter complex to the 3' pre-attached adapter of the same post-association single stranded cDNA template, wherein each adapter complex comprises at least one oligonucleotide;
(v) ligating an oligonucleotide from the 5' adapter complex to the 5' pre-attached adapter of the post-association single stranded cDNA template and ligating an oligonucleotide from the 3' adapter complex to the 3' pre-attached adapter of the same post-association single stranded cDNA template; and
(vi) selectively amplifying the cDNA sample using primers specific to the ligated oligonucleotides.

In one embodiment:
(A) the 5' adapter complex is a front oligonucleotide dimer comprising:
  (i) a front lig-oligonucleotide for ligating to the 5' pre-attached adapter of the post-association single stranded cDNA template; and
  (ii) a front link-oligonucleotide for annealing to the 5' pre-attached adapter and the front lig-oligonucleotide, the front link-oligonucleotide comprising a region complementary to the 5' pre-attached adapter and a region complementary to the front lig-oligonucleotide,
  such that, on annealing, an end of the front lig-oligonucleotide is adjacent an end of the 5' pre-attached adapter to enable ligation of the front lig-oligonucleotide to the 5' pre-attached adapter at a ligation site; and
(B) the 3' adapter complex is a back oligonucleotide dimer comprising:
  (i) a back lig-oligonucleotide for ligating to the 3' pre-attached adapter of the post-association single stranded cDNA template; and
  (ii) a back link-oligonucleotide for annealing to the 3' pre-attached adapter and the back lig-oligonucleotide, the back link-oligonucleotide comprising a region complementary to the 3' pre-attached adapter and a region complementary to the back lig-oligonucleotide,
  such that, on annealing, an end of the back lig-oligonucleotide is adjacent an end of the 3' pre-attached adapter to enable ligation of the back lig-oligonucleotide to the 3' pre-attached adapter at a ligation site.

Suitably:
(A) the front link-oligonucleotide comprises:
  (i) a template overhang region at an end of the front link-oligonucleotide proximal the region complementary to the 5' pre-attached adapter, the template overhang region being non-complementary to a corresponding region of the post-association single stranded cDNA template; and/or
  (ii) a lig-oligonucleotide overhang region at an end of the front link-oligonucleotide proximal the region complementary to the front lig-oligonucleotide, the lig-oligonucleotide overhang region being non-complementary to a corresponding region of the front lig-oligonucleotide; and/or
(B) the back link-oligonucleotide comprises:
  (i) a template overhang region at an end of the back link-oligonucleotide proximal the region complementary to the 3' pre-attached adapter, the template overhang region being non-complementary to a corresponding region of the post-association single stranded cDNA template; and/or
(ii) a lig-oligonucleotide overhang region at an end of the back link-oligonucleotide proximal the region complementary to the back lig-oligonucleotide, the lig-oligonucleotide overhang region being non-complementary to a corresponding region of the back lig-oligonucleotide.

Suitably, the template overhang and/or lig-oligonucleotide overhang is between about 1 bp and about 20 bp in length. The template overhang and/or lig-oligonucleotide overhang may be between 2 bp and 19 bp, between 3 bp and 18 bp, between 2 bp and 17 bp, between 3 bp and 16 bp, between 2 bp and 15 bp, between 3 bp and 14 bp, between, 2 bp and 13 bp, between 3 bp and 12 bp, between 2 bp and 11 bp, between 3 bp and 10 bp, between 2 bp and 9 bp, between 3 bp and 8 bp, between 2 bp and 7 bp, between 3 bp and 6 bp, between 2 bp and 5 bp, between 3 bp and 5 bp or between 2 bp and 4 bp. Preferably, the template overhang and/or lig-oligonucleotide overhang is 3 bp.

The template overhang and/or lig-oligonucleotide overhang may be at least 2 bp, or at least 3 bp. Preferably, the template overhang and/or lig-oligonucleotide overhang is at least 3 bp.

Suitably, a combined length of the front link-oligonucleotide and the front lig-oligonucleotide is less than about 300 bp and/or a combined length of the back link-oligonucleotide and the back lig-oligonucleotide is less than about 300 bp.

Suitably, the front and/or back link-oligonucleotide has a length of less than 200 bp.

Suitably, the front oligonucleotide dimer and/or the back oligonucleotide dimer has at least one non-blunt end.

Suitably, the front link-oligonucleotide and/or the back link-oligonucleotide provides at least 5 bp of complementary binding either side of the ligation site.

Suitably, a nucleotide sequence of the front oligonucleotide dimer is different and non-complementary to a nucleotide sequence of the back oligonucleotide dimer.

Suitably, at least one of the front oligonucleotide dimer and the back oligonucleotide dimer is annealable to the post-association single stranded cDNA template at a temperature of over 30° C.

Suitably, a concentration of the front oligonucleotide dimer and/or a concentration of the back oligonucleotide dimer exceeds a concentration of a predicted total single stranded cDNA concentration or total cDNA in the cDNA sample.

Suitably, the step of re-associating the cDNA sample has a duration of 0-24 hours, optionally 0-8 hours, 1-7 hours, 1-24 hours or 7-24 hours.

In a second aspect, the present invention provides an oligonucleotide dimer composition for use in a method as described above for selective amplification of single stranded cDNA by ligation of an oligonucleotide to a 5' and a 3' end of a post-association single stranded cDNA template having known 5' and 3' pre-attached adapters, wherein the composition comprises:
(A) a front oligonucleotide dimer comprising:
    (i) a front lig-oligonucleotide for ligating to the 5' pre-attached adapter of the post-association single stranded cDNA template; and
    (ii) a front link-oligonucleotide for annealing to the 5' pre-attached adapter and the front lig-oligonucleotide, the front link-oligonucleotide comprising a region complementary to the 5' pre-attached adapter and a region complementary to the front lig-oligonucleotide,
    such that, on annealing, an end of the front lig-oligonucleotide is adjacent an end of the 5' pre-attached adapter to enable ligation of the front lig-oligonucleotide to the 5' pre-attached adapter at a ligation site; and
(B) a back oligonucleotide dimer comprising:
    (i) a back lig-oligonucleotide for ligating to the 3' pre-attached adapter of the post-association single stranded cDNA template; and
    (ii) a back link-oligonucleotide for annealing to the 3' pre-attached adapter and the back lig-oligonucleotide, the back link oligonucleotide comprising a region complementary to the 3' pre-attached adapter and a region complementary to the back lig-oligonucleotide,
    such that, on annealing, an end of the back lig-oligonucleotide is adjacent an end of the 3' pre-attached adapter to enable ligation of the back lig-oligonucleotide to the 3' pre-attached adapter at a ligation site.

In one embodiment:
(A) the front link-oligonucleotide comprises:
    (i) a template overhang region at an end of the front link-oligonucleotide proximal the region complementary to the 5' pre-attached adapter, the template overhang region being non-complementary to a corresponding region of the post-association single stranded cDNA template; and/or
    (ii) a lig-oligonucleotide overhang region at an end of the front link-oligonucleotide proximal the region complementary to the front lig-oligonucleotide, the lig-oligonucleotide overhang region being non-complementary to a corresponding region of the front lig-oligonucleotide; and/or
(B) the back link-oligonucleotide comprises:
    (i) a template overhang region at an end of the back link-oligonucleotide proximal the region complementary to the 3' pre-attached adapter, the template overhang region being non-complementary to a corresponding region of the post-association single stranded cDNA template; and/or
    (ii) a lig-oligonucleotide overhang region at an end of the back link-oligonucleotide proximal the region complementary to the back lig-oligonucleotide, the lig-oligonucleotide overhang region being non-complementary to a corresponding region of the back lig-oligonucleotide.

Suitably, the template overhang and/or lig-oligonucleotide overhang is between about 1 bp and about 20 bp in length. The template overhang and/or lig-oligonucleotide overhang may be between 2 bp and 19 bp, between 3 bp and 18 bp, between 2 bp and 17 bp, between 3 bp and 16 bp, between 2 bp and 15 bp, between 3 bp and 14 bp, between, 2 bp and 13 bp, between 3 bp and 12 bp, between 2 bp and 11 bp, between 3 bp and 10 bp, between 2 bp and 9 bp, between 3 bp and 8 bp, between 2 bp and 7 bp, between 3 bp and 6 bp, between 2 bp and 5 bp, between 3 bp and 5 bp or between 2 bp and 4 bp. Preferably, the template overhang and/or lig-oligonucleotide overhang is 3 bp.

The template overhang and/or lig-oligonucleotide overhang may be at least 2 bp, or at least 3 bp. Preferably, the template overhang and/or lig-oligonucleotide overhang is at least 3 bp.

Suitably, a combined length of the front link-oligonucleotide and the front lig-oligonucleotide is less than about 300 bp and/or a combined length of the back link-oligonucleotide and the back lig-oligonucleotide is less than about 300 bp.

Suitably, the front and/or back link-oligonucleotide has a length of less than 200 bp.

Suitably, the front oligonucleotide dimer and/or the back oligonucleotide dimer has at least one non-blunt end.

Suitably, in use of the composition, the front link-oligonucleotide and/or the back link-oligonucleotide provides at least 5 bp of complementary binding either side of the ligation site.

Suitably, a nucleotide sequence of the front oligonucleotide dimer is different and non-complementary to a nucleotide sequence of the back oligonucleotide dimer.

Suitably, the front oligonucleotide dimer and/or the back oligonucleotide dimer is annealable to the post-association single stranded cDNA template at a temperature of over 30° C.

A further aspect of the present invention provides use of a method as described above or an oligonucleotide dimer composition as described above in a process of RNA or DNA sequencing, optionally for discovery of new RNA and/or detection of low abundance RNA, further optionally wherein the sequencing is single cell sequencing.

A further aspect of the present invention provides use of a method as described above or an oligonucleotide dimer composition as described above in a process of metagenomic sequencing for discovery of new microbes and/or detection of low abundance microbes.

A further aspect of the present invention provides use of a method as described above or an oligonucleotide dimer composition as described above in a process of screening DNA or RNA samples, or screening genetic samples for the presence of infectious diseases.

A further aspect of the present invention provides use of a method as described above or an oligonucleotide dimer composition as described above in a process of detecting a nucleic acid biomarker, optionally a disease biomarker, further optionally a cancer biomarker.

In particular embodiments, according to all aspects of the invention, the method further comprises reporting the result. The result may be in the form of an RNA or DNA sequence, an indication of the presence or absence of a microbe or disease and/or an indication of the presence or absence or level of a disease biomarker.

A further aspect of the present invention provides a selective amplification kit for selectively amplifying low abundance cDNA from a cDNA sample and/or for selective amplification of cDNA comprising known adapter sequences, the cDNA sample comprising cDNA templates having known 5' and 3' pre-attached adapters, the kit comprising means for preparing an oligonucleotide dimer composition as described above and means for implementing the method of selective amplification as described above. In particular embodiments, the means for preparing an oligonucleotide dimer composition may comprise a front lig-oligonucleotide, a front link-oligonucleotide, a back lig-oligonucleotide and/or a back link-oligonucleotide as described herein. In further embodiments, the means for preparing an oligonucleotide dimer composition may comprise a front oligonucleotide dimer and/or a back oligonucleotide dimer as described herein.

The means for implementing the method of selective amplification may comprise primers specific to the front and/or back lig-oligonucleotides.

In particular embodiments, the kit may further comprise a hybridization buffer. The hybridization buffer may comprise HEPES 1M (pH=7.5), NaCl 5M and $H_2O$. The kit may also comprise ligase and/or ligase buffer. Any suitable ligase may be used. The ligase may be a nick repair ligase or a blunt end ligase. Optionally, the ligase may be Taq DNA ligase. Suitable ligase buffers are also well known and commercially available In further embodiments, the kit may further comprise primers for adding phosphate groups to cDNA prior to its use as a cDNA sample. These primers are based on the known 5' pre-attached adapter and known 3' pre-attached adapter sequences.

In particular embodiments, the kit may further comprise suitable reagents for PCR including one or more, up to all, of a polymerase, dinucleotide triphosphates (dNTPs), $MgCl_2$ and buffer. Any suitable polymerase may be utilised. Generally, DNA polymerases are used to amplify nucleic acid targets according to the invention. Examples include thermostable polymerases such as Taq or Pfu polymerase and the various derivatives of those enzymes. Suitable buffers are also well known and commercially available and may be included in a PCR mastermix that includes the majority of the components required for PCR amplification.

In further embodiments, the kit may further comprise suitable reagents for reverse transcription of RNA to cDNA including a reverse transcriptase enzyme. Any suitable reverse transcriptase may be utilised. Suitable buffers are also well known and commercially available and may be included in a reverse transcription mastermix that includes the majority of the components required for reverse transcription.

A further aspect of the present invention provides a set of reagents for use in a method as described herein, comprising:
 a front lig-oligonucleotide, a front link-oligonucleotide, a back lig-oligonucleotide and/or a back link-oligonucleotide; and
 primers specific to the front and/or back lig-oligonucleotides.

The front lig-oligonucleotide, front link-oligonucleotide, back lig-oligonucleotide and/or back link-oligonucleotide may be provided as an oligonucleotide dimer composition as described herein.

The set of reagents may further comprise one or more up to all of the following: a hybridization buffer (optionally comprising HEPES 1M (pH=7.5), NaCl 5M and $H_2O$), a ligase, a ligase buffer, a primer pair for adding phosphate groups to cDNA, a DNA polymerase and/or dNTPs.

In an embodiment, the set of reagents comprises:
 a front lig-oligonucleotide, a front link-oligonucleotide, a back lig-oligonucleotide and/or a back link-oligonucleotide;
 primers specific to the front and/or back lig-oligonucleotides;
 a hybridization buffer;
 a ligase;
 a ligase buffer; and
 a primer pair for adding phosphate groups to cDNA.

Another important aspect of the present method is the ability to select cDNA having known adapter sequences. This aspect could be applied for single cell sequencing where adapters are necessary for assigning reads to individual cells. In this application, cDNA sequences without cell identifying barcodes/adapters arise within the cDNA library. These are known as template switching oligo (TSO) artefacts and are undesirable in single cell sequencing projects due to not being assignable to a cell of origin. The present method can be applied to only select for cDNA sequences with the desired adapter sequences thus effectively limiting the sequencing of TSO artefacts. The present method can also be performed with single cell cDNA libraries to both remove TSO artefacts and to improve transcriptome coverage per cell.

TSO clean-up takes place when the methods of the invention are used for normalization of a cDNA sample. However, TSO clean-up can also be carried out without normalization in which case it is not necessary to include a step of re-associating the cDNA sample to produce a mixture of post-association single stranded cDNA templates and post-association double stranded cDNA templates.

Thus, according to a further aspect of the present invention there is provided a method of selective amplification of cDNA comprising known adapter sequences, the method comprising:
 (i) providing a cDNA sample comprising double stranded cDNA templates, a portion of the templates having a known 5' pre-attached adapter and a known 3' pre-attached adapter;
 (ii) denaturing the cDNA sample to produce single stranded cDNA templates;
 (iii) annealing a 5' adapter complex to the 5' pre-attached adapter of at least one single stranded cDNA template, and annealing a 3' adapter complex to the 3' pre-attached adapter of the same single stranded cDNA template, wherein each adapter complex comprises at least one oligonucleotide;
 (v) ligating an oligonucleotide from the 5' adapter complex to the 5' pre-attached adapter of the single stranded cDNA template and ligating an oligonucleotide from the 3' adapter complex to the 3' pre-attached adapter of the same single stranded cDNA template; and
 (vi) selectively amplifying the cDNA sample using primers specific to the ligated oligonucleotides.

The embodiments of the method of selective amplification of single stranded cDNA recited above apply mutatis mutandis to the method of selective amplification of cDNA comprising known adapter sequences and are not repeated for reasons of conciseness. The oligonucleotide dimer composition is suitable for use in a method as defined herein for selective amplification of cDNA comprising known adapter sequences. The method of selective amplification of cDNA comprising known adapter sequences as defined herein can be used in a process of RNA or DNA sequencing, optionally for discovery of new RNA and/or detection of low abundance RNA, further optionally wherein the sequencing is single cell sequencing. Likewise, the method can be used in a process of metagenomic sequencing for discovery of new microbes and/or detection of low abundance microbes, in a process of screening DNA or RNA samples, or screening genetic samples for the presence of infectious diseases or in a process of detecting a nucleic acid biomarker, optionally a disease biomarker, further optionally a cancer biomarker. The kits and sets of reagents defined herein are also suitable for use in the method for selective amplification of cDNA comprising known adapter sequences.

In some embodiments, according to all aspects of the invention, the cDNA sample comprises no more than 700 ng, 500 ng, 100 ng, 20 ng, 10 ng, 5 ng or 1 ng of starting cDNA. The cDNA sample may comprise 1-500 ng, 5-100 ng, or 10-50 ng of starting cDNA.

In particular embodiments, according to all aspects of the invention, RNA from a sample is firstly reverse transcribed to cDNA. Sample types include blood samples (in particular from plasma, and also serum), other bodily fluids such as saliva, urine or lymph fluid. Other sample types include solid tissues, including frozen tissue or formalin fixed, paraffin embedded (FFPE) material. The RNA may be messenger RNA (mRNA), microRNA (miRNA) etc. In such embodiments, the RNA is typically reverse transcribed using a reverse transcriptase enzyme to form a complementary DNA (cDNA) molecule. Methods for reverse transcribing RNA to cDNA using a reverse transcriptase are well-known in the art. Any suitable reverse transcriptase can be used, examples of suitable reverse transcriptases being widely available in the art. The initial cDNA molecule may be single stranded until DNA polymerase has been used to generate the complementary strand. Commercially available kits (such as NEBNext Single Cell/Low Input cDNA Synthesis & Amplification Module) can be used to convert RNA into double stranded cDNA with 5' and 3' adapters. Primers based on the 5' and 3' adapters can be used to add phosphate groups to the cDNA. A cDNA purification step (for example with ProNex or Ampure beads) may be carried out prior to use of the cDNA as a cDNA sample.

As the present invention only requires a low amount of starting cDNA, this can be produced from a small quantity of RNA and/or without the requirement for additional PCR cycles during the generation of the cDNA. The RNA sample may comprise no more than 3 µg, 2 µg, 1 µg, 500 ng, 100 ng, 10 ng or 1 ng of starting RNA. The RNA sample may comprise 1 ng-3 µg, 10 ng-2 µg, or 100 ng-1 µg of starting RNA.

DETAILED DESCRIPTION

The above and other aspects of the present invention will now be described in further detail, by way of example only, with reference to the following examples and the accompanying figures, in which.

Figure 1:
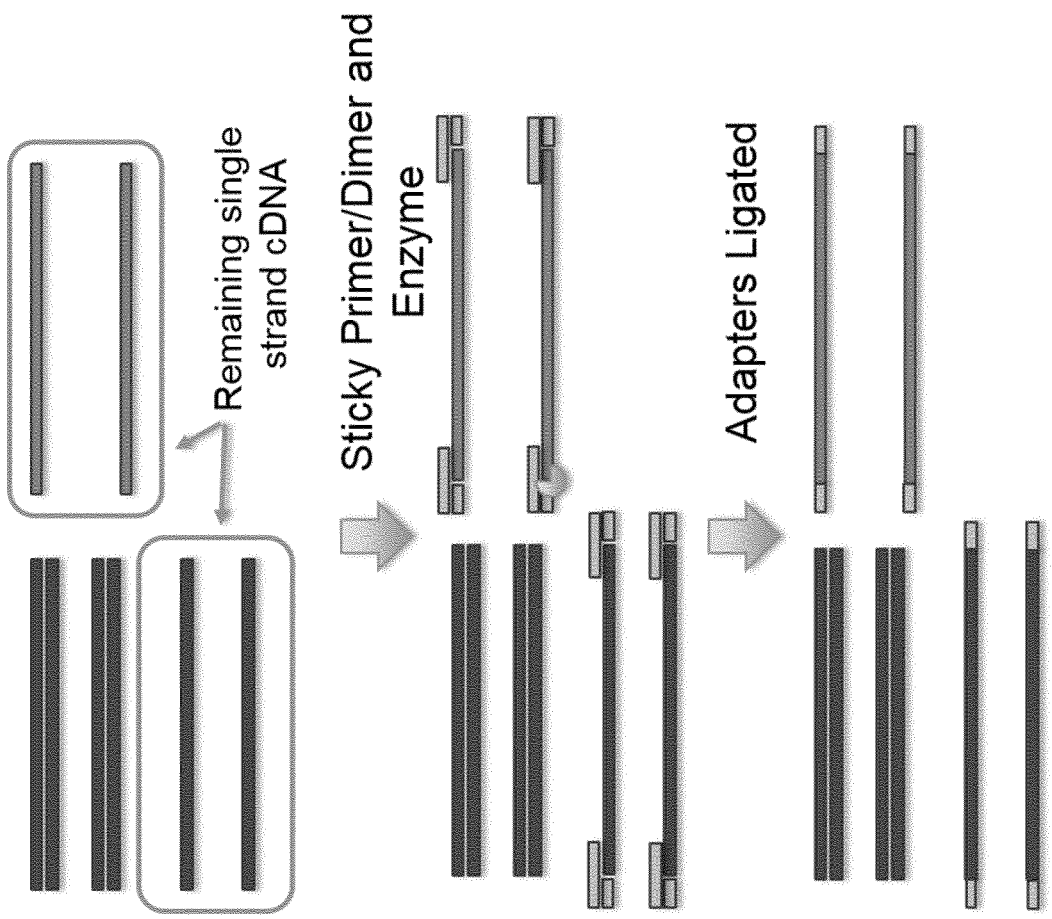
FIG. 1 is a schematic overview showing addition of ligation sequences to the ends of single stranded cDNA templates.

To address issues in current cDNA normalization technology, the present inventors have developed an improved selective amplification method. The present method utilises the same denaturation and re-hybridization process as the DSN and column methods described above. However, the present method differs from current approaches by using a non-depletion or additive mechanism. In other words, the present invention provides a method and means for increasing the amount of low abundance cDNA in a sample. These methods and means can be used for cDNA normalization in sequencing processes or for other processes that would benefit from amplification of low abundance cDNA, such as discovery, detection or identification of microbes or biomarkers.

In the context of the present invention, the following explanations of terms and methods are provided to better describe the present disclosure and to provide guidance in the practice of the present disclosure.

The phrase 'selective amplification' is used to describe the method developed by the present inventors of amplification of particular DNA templates in preference to other DNA templates, for example, amplification of only single stranded cDNA in a sample that comprises a mixture of single stranded and double stranded cDNA. The term is also used herein to describe preferentially amplifying a particular category of DNA, such as low abundance DNA.

The term 'adapter' is used to describe a short DNA sequence added to an end of a DNA template, such as those commonly used in RNA sequencing by ligating an adapter to a cDNA template. A '3' pre-attached adapter' refers to an adapter having a known nucleotide sequence that has been added to the 3' end of a cDNA template. A '5' pre-attached adapter' refers to an adapter having a known nucleotide sequence that has been added to the 5' end of a cDNA template.

The terms 'normalized' and 'normalized fraction' refer to the process of levelling the abundance of different transcripts within a sample. This can be achieved by prior art methods of reducing the amount of highly abundant transcripts, or by using the methods of the present invention to selectively amplify low abundance transcripts.

The phrase 'post-association single stranded cDNA template' as used in the context of the present invention, refers to a single stranded cDNA template that has been generated by dis-associating and re-associating (i.e., denaturing and re-hybridizing) a sample of double stranded cDNA to form a mixture of single stranded cDNA and double stranded cDNA. The single stranded cDNA that remains single stranded after re-association is referred to as post-association single stranded cDNA. If a re-association step is not carried out, the phrase 'post-association single stranded cDNA template' is interchangeable with 'single stranded cDNA template' in the embodiments defined herein.

The phrase 'ligated-adapter-cDNA template' as used herein, refers to a cDNA template formed by ligation of an adapter to a cDNA template.

The present invention encompasses an 'adapter complex' which is suitable for annealing to an end of a post-association single stranded cDNA template. The term 'adapter complex' refers to an adapter that comprises more than one component.

The terms 'front oligonucleotide dimer', 'front k-linker' and 'front dimer' as used in the context of the present invention, refer to an adapter complex that can be annealed to the 5' end of a post-association single stranded cDNA template. The terms 'back oligonucleotide dimer', 'back k-linker' and 'back dimer', as used in the context of the present invention, refer to an adapter complex that can be annealed to the 3' end of a post-association single stranded cDNA template.

The terms 'front lig-oligonucleotide' and 'front lig' as used in the context of the present invention, refer to an oligonucleotide component of the front dimer. The terms 'back lig-oligonucleotide' or 'back lig' as used in the context of the present invention, refer to an oligonucleotide component of the back dimer.

The terms 'front link-oligonucleotide' and 'front link' as used in the context of the present invention, refer to an oligonucleotide component of the front dimer. The terms 'back link-oligonucleotide' and 'back link' as used in the context of the present invention, refer to an oligonucleotide component of the back dimer.

The term 'overhang' is used in the context of the present invention to describe an overhanging region of the sequence of the dimer of the present invention, where the overhanging region is non-complementary to the region with which it is paired, once annealed to a post-association single stranded cDNA template, such that the overhanging region does not bind with its paired region.

The single stranded cDNA is selectively amplified using primers specific to the ligated oligonucleotides. As single stranded DNA is the template, the primer region of one primer of a specific primer pair is complementary to the single stranded DNA molecule. The other primer of the specific primer pair comprises a primer region which is complementary to, and therefore hybridises with, the complementary single stranded DNA molecule formed during an amplification cycle. Thus, one primer is complementary to one of the ligated oligonucleotides and the other primer comprises (at least partially) the sequence of the other ligated oligonucleotide.

Column Method

As described above the hydroxyapatite column method relies on the denaturation and re-hybridization of cDNA strands. As the single stranded cDNA move about in solution, the sequences that are more highly abundant have a greater probability of finding a matching complementary sequence with which to re-hybridize. In the column method, the denatured and re-hybridized cDNA library is passed through a heated column filled with hydroxyapatite granules. The hydroxyapatite preferentially binds to larger DNA molecules. Since the single stranded cDNA will be roughly one half the size of the re-hybridized cDNA, elution of the single stranded fraction can be managed if the mean cDNA sequence length is known. The resulting elution is intended to be enriched for the single stranded cDNA which are then amplified using PCR.

The hydroxyapatite column method was carried out as described in Andrews-Pfannkoch et al. (Andrews-Pfannkoch, C., Fadrosh, D. W., Thorpe, J. & Williamson, S. J. Hydroxyapatite-mediated separation of double-stranded DNA, single-stranded DNA, and RNA genomes from natural viral assemblages. Appl. Environ. Microbiol. 76, 5039-5045 (2010) with 4 µg cDNA starting sample. The hydroxyapatite column method did not produce usable yield when used with 2 µg or less of cDNA.

As the column method is based on separation by size this method results in a loss of representation for longer RNA sequences (longer than 4 kb) which is observable in the length distribution before and after normalization.

DSN Method

As for the column method, the DSN method relies on the denaturation and re-hybridization of cDNA strands. As the single stranded cDNA move about in solution, the sequences that are more highly abundant have a greater probability of finding a matching complementary sequence with which to re-hybridize. In the DSN method, an enzyme which specifically cleaves double stranded DNA is used to decompose all double stranded cDNA within the solution.

The commercially available Evrogen Trimmer-2 cDNA normalization kit uses the DSN method. This kit was used according to the manufacturer's instructions with 1 µg cDNA starting sample. However, to produce enough material for long read RNA sequencing it was found necessary to use 2 µg of cDNA.

The DSN method was found to completely eradicate high abundance RNAs and this would also be expected to be the case for RNAs with sequence similarity to the high abundance RNAs. Thus, over-depletion was observed in which high abundance RNAs were not just reduced in quantity but were completely removed from the samples. Table 1 illustrates over-depletion of ranks 1-20 and shows a selection of lower ranks (55, 64, 77, 92 and 98) in which the RNAs were significantly reduced but not completely depleted.

TABLE 1 over-depletion of high abundance RNAs with DSN method

| Rank | Ensembl Transcript ID | Standard Read Count | DSNase Read Count |
| --- | --- | --- | --- |
| 1 | ENSGALT00000023323 | 18937 | 0 |
| 2 | ENSGALT00000039524 | 14928 | 0 |
| 3 | ENSGALT00000052417 | 9147 | 0 |
| 4 | ENSGALT00000022187 | 4293 | 0 |
| 5 | ENSGALT00000011687 | 3822 | 0 |
| 6 | ENSGALT00000041222 | 3610 | 0 |
| 7 | ENSGALT00000016648 | 2996 | 0 |
| 8 | ENSGALT00000044106 | 2949 | 0 |
| 9 | ENSGALT00000084298 | 2825 | 0 |
| 10 | ENSGALT00000023065 | 2677 | 0 |
| 11 | ENSGALT00000088434 | 2255 | 0 |
| 12 | ENSGALT00000011524 | 2151 | 0 |
| 13 | ENSGALT00000055441 | 2127 | 0 |
| 14 | ENSGALT00000044027 | 2080 | 0 |
| 15 | ENSGALT00000078059 | 2052 | 0 |
| 16 | ENSGALT00000084500 | 2020 | 0 |
| 17 | ENSGALT00000071026 | 1839 | 0 |
| 18 | ENSGALT00000015018 | 1742 | 0 |
| 19 | ENSGALT00000046070 | 1731 | 0 |
| 20 | ENSGALT00000014652 | 1718 | 0 |
| 55 | ENSGALT00000066490 | 649 | 1 |
| 64 | ENSGALT00000087166 | 630 | 5 |
| 77 | ENSGALT00000072914 | 565 | 1 |
| 92 | ENSGALT00000043160 | 475 | 1 |
| 98 | ENSGALT00000070660 | 451 | 2 |

In addition, the DSN method creates conditions in which artificial chimeric sequences can be generated, which can show up as false positives for gene predictions.

Selective Amplification Method

Figure 2:
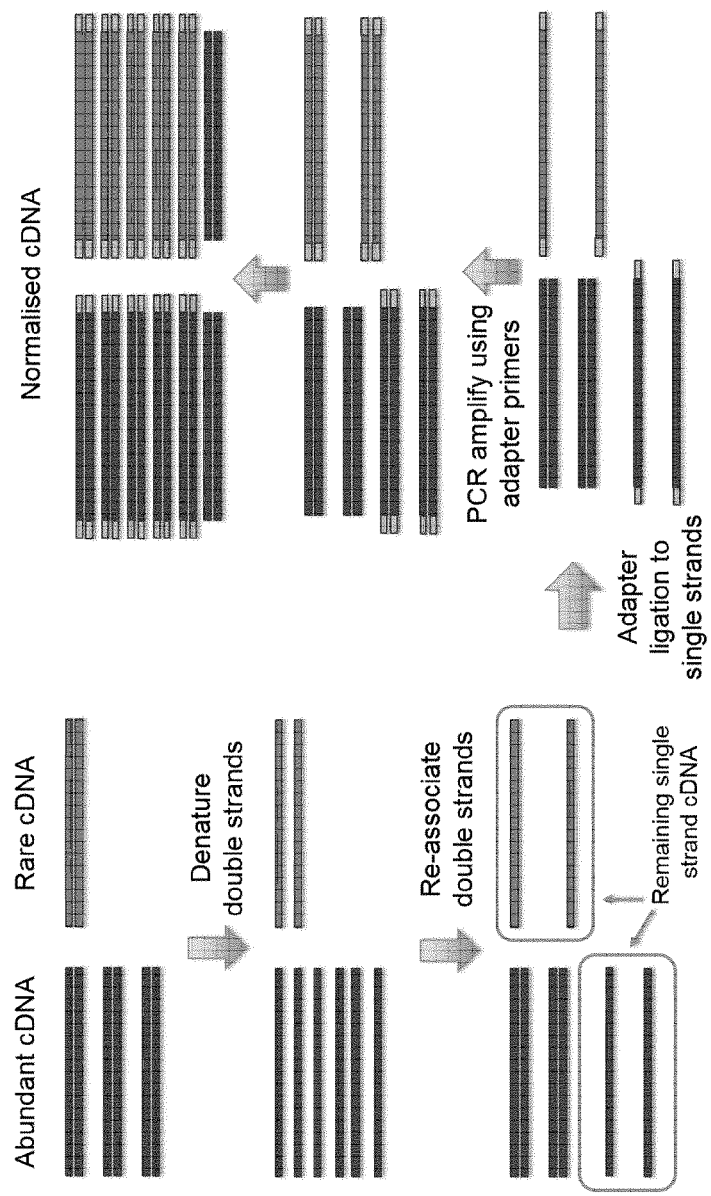
FIG. 2 is a schematic overview of an embodiment of a cDNA normalization process in accordance with the present invention.
Figure 3:
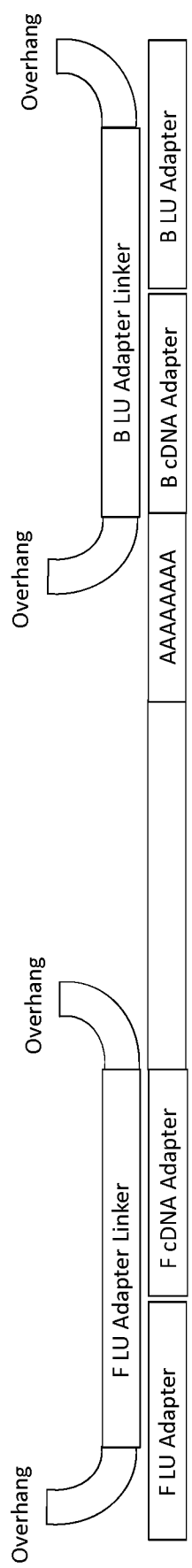
FIG. 3 is a schematic overview of Front and Back oligonucleotide dimer structures as shown annealed to single strand cDNA template.

The present method is illustrated in FIGS. 1 to 3. In overview, with reference to FIG. 2, a cDNA sample, comprising cDNA having known 5' and 3' pre-attached adapters, is denatured to provide a single stranded cDNA sample; the sample is then re-hybridised or re-associated to provide a mixture of single and double stranded cDNA. This single stranded cDNA represents the low abundance cDNA. The single stranded cDNA within the re-associated sample is then modified by adding oligonucleotides to the 5' and 3' pre-attached adapters. The cDNA sample is amplified using primers to these oligonucleotides. This process selectively increases the content of only the single stranded cDNA within the re-associated sample, thereby increasing the content of the low abundance cDNA in the sample, thereby providing a normalized sample.

The input cDNA library for the selective amplification method is double-stranded and the double stranded templates each comprise a 5' pre-attached adapter of known nucleotide sequence and a 3' pre-attached adapter of known nucleotide sequence. Since the present method is an additive method, lower quantities of starting cDNA are required as compared to prior art normalization methods. In the DSNase method, a minimum of 1 μg of input cDNA is required and in the column method a minimum of 4 μg of input cDNA is required. In testing, it was found that the present method could be applied with as little as 20 ng of starting cDNA.

The first stage of the present method involves combining the input cDNA with a hybridization buffer and heating the solution to denaturation temperatures—which is about 98 degrees Celsius, to produce denatured single stranded cDNA templates. After 5-10 minutes, the solution is then brought down to re-hybridization temperature—about 68 degrees Celsius. The solution is incubated at this temperature for between 0-24 hours depending on the amount of normalization required. 7 hours is a typical duration for the re-association step. This step produces a re-associated or re-hybridised sample comprising post-association double stranded cDNA templates and post-association single stranded cDNA templates.

After incubation, oligonucleotide dimers (termed K-linkers by the present inventors), of the present invention are added. These oligonucleotide dimers are discussed in more detail below. At this point, the solution can be left to incubate at 68 degrees Celsius from 0-1 hour. 5 minutes is a typical duration for this incubation step. The solution is then brought down to the annealing temperatures of the K-linkers, which is typically between 40-60 degrees Celsius, for example 44 degrees celsius. The solution is incubated at the temperature from between 10 minutes-2 hours, for example 25 minutes. This step anneals the K-linkers to the post-association single stranded cDNA templates.

After this incubation period, DNA ligase is added together with ligation mix. The solution is incubated at this same temperature for 0.5-2 hours, for example 1 hour, and then brought down to room temperature. This step results in formation of ligated-adapter-cDNA templates where an oligonucleotide from a K-linker is ligated to each end of a post-association single stranded cDNA template. At this point, the cDNA may be purified (for example using Pronex or Ampure beads) or may be used directly for PCR amplification using primers based on the K-linker sequences.

After PCR amplification, the cDNA is then purified using any appropriate means and the resultant cDNA represents the normalized cDNA library.

The post-association double stranded cDNA templates can be removed before PCR amplification but, after testing, the present inventors have shown that leaving the double stranded cDNA in the solution does not negatively impact the normalization process. Indeed the post-association double stranded cDNA can also be analysed and used, for example, to attain estimates of gene expression. This involves an additional (PCR) selective amplification step using primers to the known 5' pre-attached adapter and known 3' pre-attached adapter, wherein molecular barcodes are included in the primers. PCR amplification using primers based on the K-linker sequences is carried out first followed by a single PCR cycle using the primers to the known 5' pre-attached adapter and known 3' pre-attached adapter. The PCR can be paused to add the further primers for the final cycle. Alternatively, the cDNA can be purified after the PCR using the primers based on the K-linker sequences and a new PCR carried out for a single cycle using the primers to the known 5' pre-attached adapter and known 3' pre-attached adapter. In both cases the product will be a mixture of two distinguishable fractions comprised of sequences originating from the post-association double stranded cDNA templates and from the post-association single stranded cDNA templates. The molecular barcode addition allows for the identification of the source molecule during sequencing analysis. This aspect of the invention may be used in multiplex sequencing.

Design of Oligonucleotide Dimer Complexes

The oligonucleotide dimer compositions of the present invention comprise front and back oligonucleotide dimers (front and back K-linkers), which both anneal to the same strand of post-association single stranded cDNA.

Figure 3A:
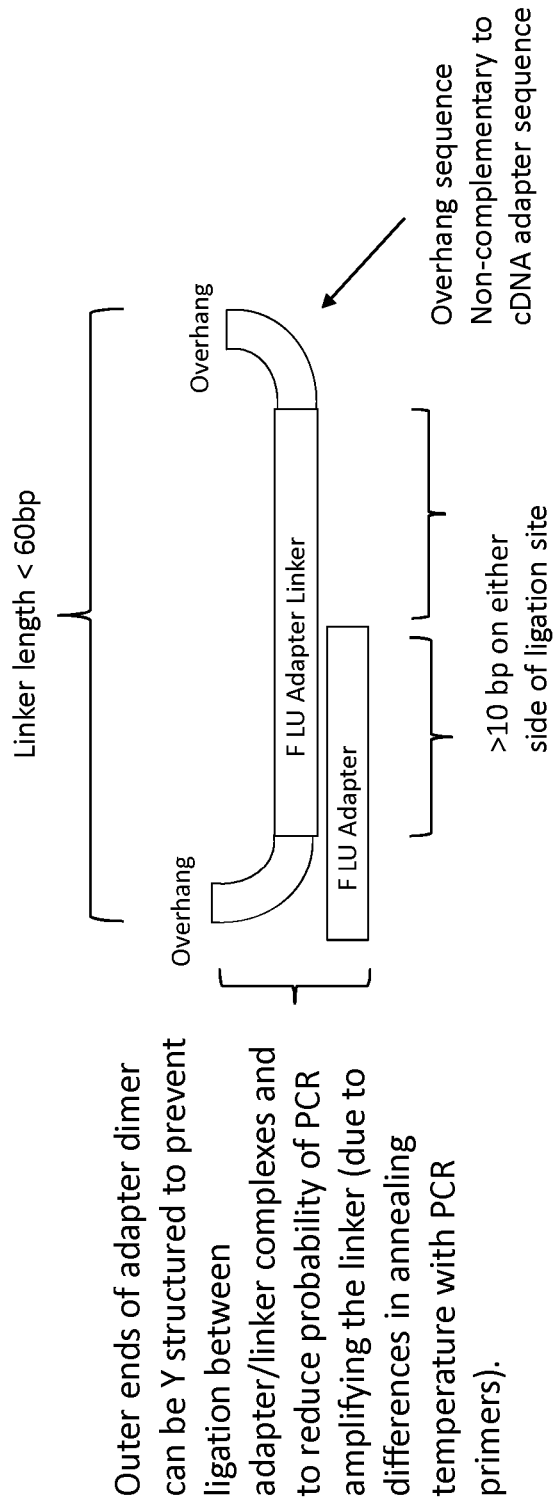
FIG. 3A is a detail thereof and FIG. 3B provides an illustration using the Example sequence representations recited herein.

With reference to FIGS. 3 and 3A, each K-linker comprises two oligonucleotide sequences; one is termed the link-oligonucleotide (also termed 'link'; termed 'LU adapter linker' in FIGS. 3 and 3A)) and the other is termed the lig-oligonucleotide (also termed 'lig'; termed 'LU adapter' in FIGS. 3 and 3A).

The link sequence includes a region complementary with the known 3'/5' pre-attached adapter sequence (that was previously added to the cDNA) and a region complementary with the lig.

As also depicted in FIGS. 3 and 3A, the link can be designed to have an overhang region at one end which is non-complementary the known pre-attached adapter sequences, this region is termed a 'template overhang'. The opposite end of the link can be provided with a similar overhang that is non-complementary to the lig sequence, this is termed a 'lig overhang' or 'lig-oligonucleotide overhang'.

The purpose of the link is to anneal to both the pre-attached adapter of the post-association single stranded cDNA template and the lig, in such a way that, in use, one end of the cDNA template is adjacent one end of the lig. By positioning the cDNA template and the lig in this way, DNA ligase can be used to ligate the cDNA template to the lig, thus adding the lig sequence to the end of the cDNA template. A lig sequence is added to both the 5' and 3' ends of the single stranded cDNA template. Front and back K-linkers are used to add these ligs to the 5' and 3' ends of the cDNA template respectively.

In the method described above, once a lig has been added to each end of the single stranded cDNA template, primers based on the sequences of the added ligs are used to selectively amplify the single stranded cDNA fraction that has successfully ligated to both front and back lig sequences. In this way, PCR can be used to amplify only the low abundance post-association single stranded cDNA fraction.

The particular structure of the K-linkers provides advantages to overall normalization performance with the front K-linker and the back K-linker having different functions provided by their specific structural characteristics.

The front K-linker which binds to the 5' end of the single strand cDNA template (shown in the figures as the reverse complement to the original RNA sequence) can be designed so that the K-linker does not act as a primer during PCR amplification.

To provide additional advantages, the front K-linker does not have a blunt end on the lig side to allow for the use of DNA ligase that can perform blunt end ligation in the selective amplification process. Providing the lig side of the K-linker complex with a non-blunt end also avoids ligation to other K-linker complexes or to the double stranded cDNA in the solution.

Since the front linker has a 5' to 3' directionality pointing away from the template, the linker itself cannot act as a primer of the template. However, in some instances, the front lig or PCR primers could potentially anneal to the linker during PCR amplification and undergo polymerase extension to take on the template side sequence of the link. Providing the link with an overhang on the template side avoids the extended lig/primer acting as a primer for the cDNA sequences which do not have the lig sequences added to their ends, i.e., the sequences that are high abundance. Accordingly, a template overhang structure for the back link can be provided.

The back K-linker which binds to the 3' end of the single stranded cDNA template (shown in the figures as the reverse complement to the original RNA sequence) can be designed so that the K-linker does not act as a primer during PCR amplification. This can be achieved using the template overhang, which is described above and illustrated in FIGS. 3 and 3A.

The back K-linker can be provided without a blunt end on the lig side for the same reason that the front K-linker can be designed to have an overhang on the lig side. If the lig side of the back K-linker complex had a blunt end, in some instances, the lig could potentially be ligated to other K-linker complexes or to the double stranded cDNA in the sample, which could result in linking of cDNA templates.

The overhangs also serve to lower the annealing temperature of the K-linker complexes so that they are less likely to act as primers for each other during PCR amplification, where higher annealing temperatures are used. Overhangs may reduce unintended priming. Additionally or alternatively, overhangs may provide an indicator that enables the measurement of the amount of unintended priming. For example, if the K-linker complexes with their overhangs are able to prime a template then it will be possible to see the overhang sequence in the sequencing data and to conclude that it was a product of un-intended priming.

All overhangs should ideally be between about 1 bp and about 20 bp, preferably 3 bp. Longer overhangs could be used but it would make the design more difficult since there are fewer sequence compositions that would prevent unintended priming as the overhangs get longer.

The complementary regions between the cDNA template and the link, and between the link and the lig should be long enough for annealing at the temperature of activity for the ligase to be used. Nick repair ligases are particularly preferred for this process which typically require about five or more complementary bases on either side of the ligation site.

The combined length of the link and corresponding lig should ideally be less than about 300 bp, preferably less than about 200 bp, to reduce carry over during the purification process.

Figure 3B:
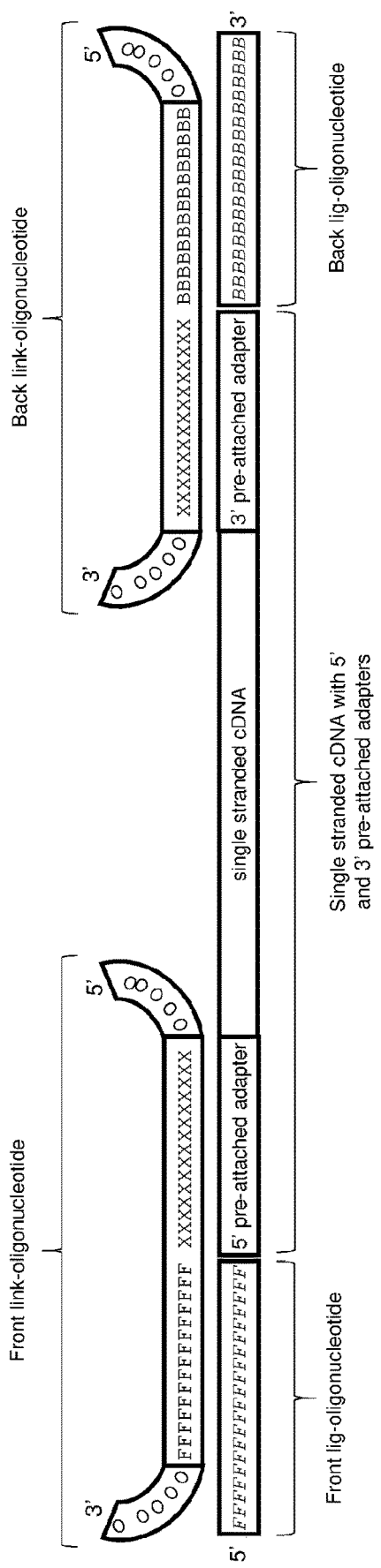

Example Sequence Representations:

All example sequence structures are provided in 5' to 3' orientation. Also illustrated in FIG. 3B.

```
Front link:
OOOOOXXXXXXXXXXXXXXXXFFFFFFFFFFFFFFFOOOOO

Front lig:
FFFFFFFFFFFFFFFFFFFF

Back link:
OOOOOBBBBBBBBBBBBBBBBBXXXXXXXXXXXXXXXXOOOOO

Back lig:
BBBBBBBBBBBBBBBBBBBB
X—Nucleotides complementary to 5'/3" pre-
attached adapter
O—Overhang sequences
F—Sequence complementary to front lig to
be ligated
F—Sequence of the front lig
B—Sequence complementary to back lig to
be ligated
B—Sequence of the back lig
```

Example of Oligonucleotides and Single Stranded cDNA Template Used in the Method:
Primer Sequences from NEB/PacBio cDNA Synthesis Kit

```
Iso-Seq Express Fwd:
                                       (SEQ ID NO: 1)
GGCAATGAAGTCGCAGGGTTG Iso-Seq Express Rev:
                                       (SEQ ID NO: 2)
AAGCAGTGGTATCAACGCAGAG Front Link:
                                       (SEQ ID NO: 3)
ATAGCGTTGATACCACTGCTTCTCACGACAGACTCGCTAA Front Lig and Primer:
                                       (SEQ ID NO: 4)
TGGACTGAT GCGAGTCTGTCGTGAG Back Link:
                                       (SEQ ID NO: 5)
AATGACGCTGGACGAACAC GGCAATGAAGTCGCAG ACA Back Lig:
                                       (SEQ ID NO: 6)
GTGTTCGTCCAGCGTC CAGGTGAGTGG Primer:
                                       (SEQ ID NO: 7)
CCACTCACCTG GACGCTGGACGAACAC
```

Overhangs are shown underlined. Regions of complementarity between oligonucleotides are shown in bold.

```
Single stranded cDNA template:
AAGCAGTGGTATCAACGCAGAGNNNNNNNNNN

NNNNNNCAACCCTGCGACTTCATTGCC
(i.e. 5-3 - sequence of 5 pre-attached
adapter, sequence of cDNA represented
by N and sequence of 3 pre-attached
adapter; regions of complementarity to
front link and back link-
oligonucleotides are shown in bold;
SEQ ID NO: 8).
```

Preparation of Oligonucleotide Dimers

Once designed, the dimers can be prepared using standard techniques well known in the art.

Amplification of Oligonucleotide-cDNA Templates

After ligation of the lig to the 3' and 5' ends of the cDNA template, the resulting solution can be purified for cDNA using an appropriate cDNA purification method. The purification step may be skipped, but skipping may result in lower efficiency for PCR amplification.

After purification or after ligation the resulting material can be PCR amplified using forward and reverse primers based on the lig sequence. The primer sequences can be chosen to have a higher annealing temperature than the complementary regions of the template/link/lig to avoid unwanted priming.

If required, the number of optimal PCR cycles can be identified by first running a qPCR experiment to identify the inflection point of the amplification curve.

The resulting cDNA from PCR amplification can then be purified and used as input for any downstream processes, such as sequencing.

Validation of the Selectively Amplified Sample

The effect of selective amplification or normalization can be indirectly measured by measuring the length distribution of the cDNA library using gel electrophoresis or directly measured using sequencing.

Figure 4:
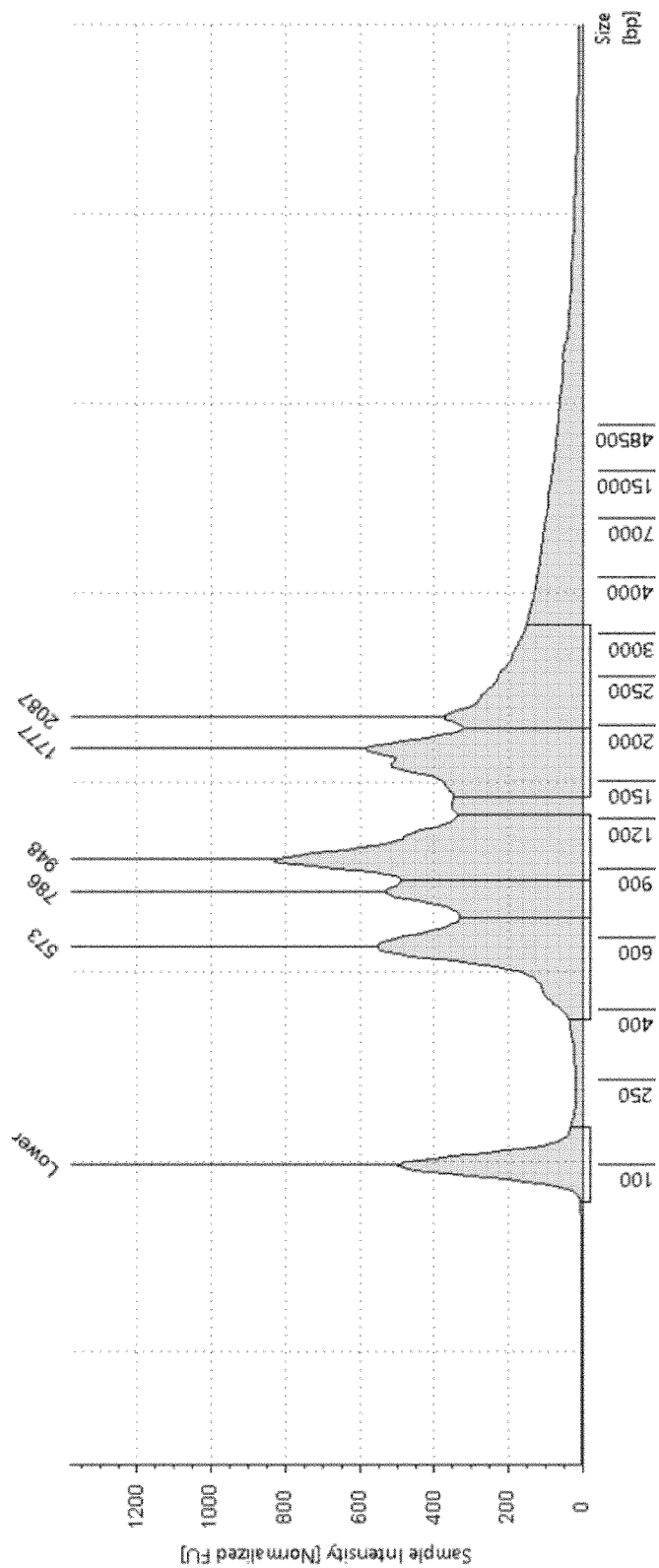
FIG. 4 is a graph showing length distribution from gel electrophoresis of input cDNA.

To identify the effect of normalization using gel electrophoresis, the length distribution plots of the input cDNA can be compared to the normalized cDNA. The input cDNA will typically show peaks along the length distribution which correspond to high abundance transcript sequences (FIG. 4).

Figure 5:
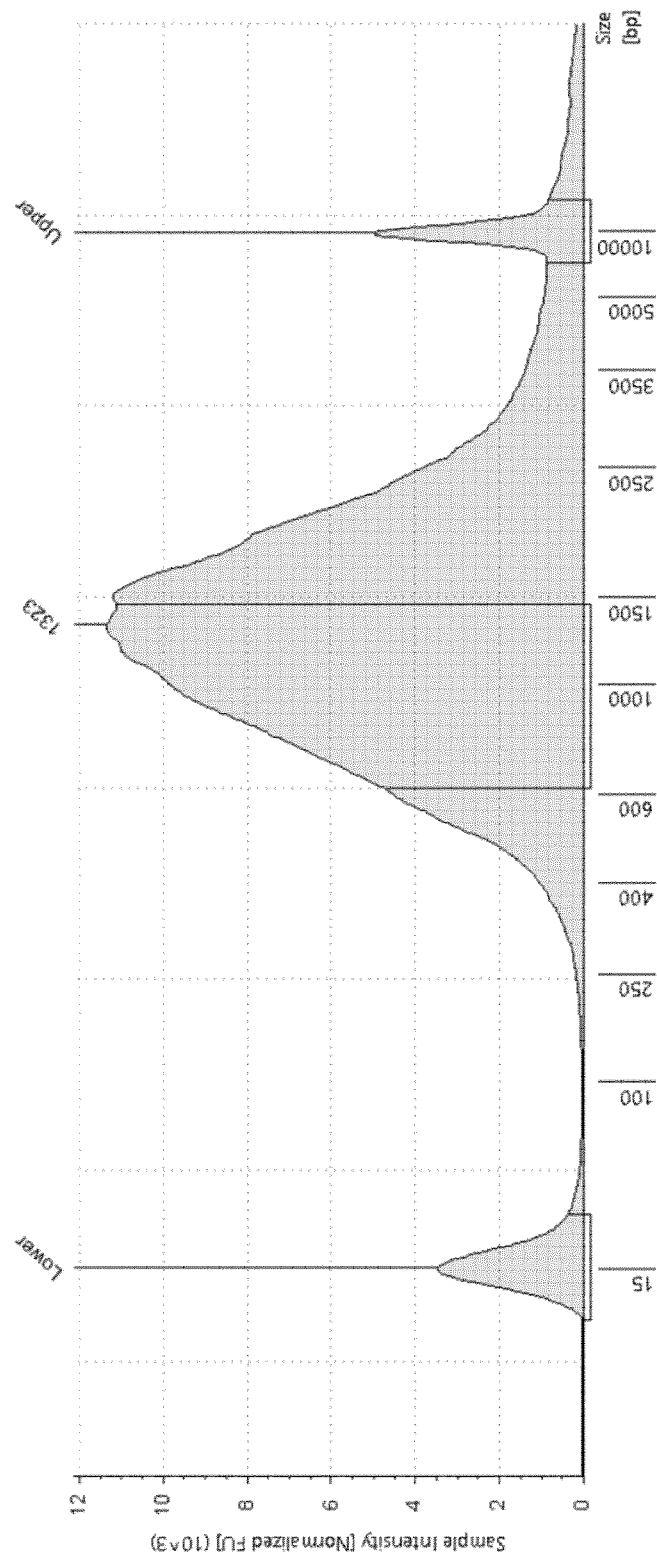
FIG. 5 is a graph showing length distribution from gel electrophoresis of normalized cDNA in resulting from an embodiment of a cDNA normalisation process in accordance with the present invention.

The normalized cDNA will have a length distribution that resembles a normal distribution with no sharp peaks (FIG. 5). This represents a uniform distribution across transcript sequences.

When using sequencing for direct measurement of normalization, the preferred method of sequencing is long read sequencing. This allows for the identification of distinct isoforms. The results for direct measurement can be either a plot of the number of reads per gene or a saturation plot showing the number of new genes identified with increase depth of sequencing.

Figure 6:
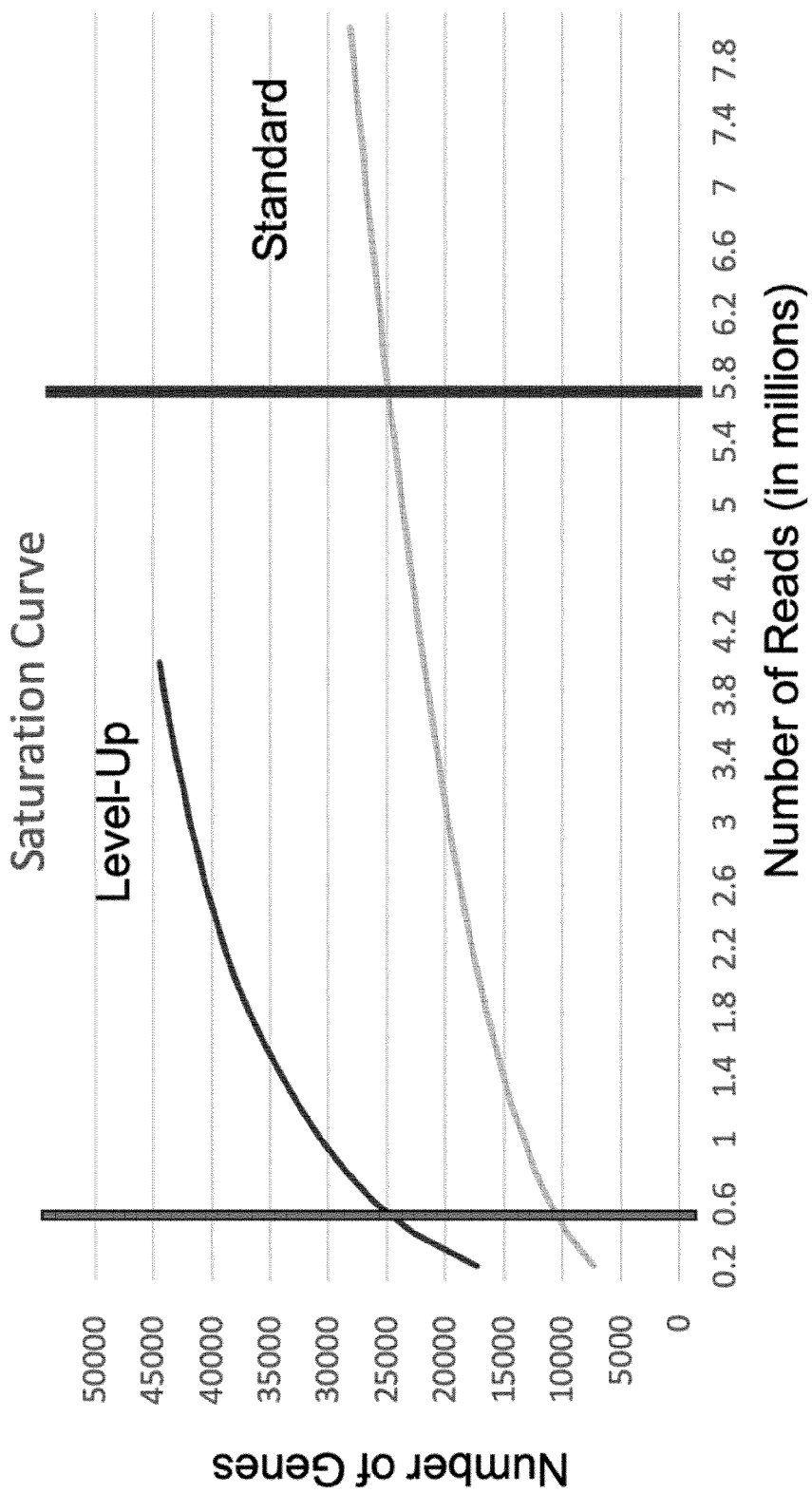
FIG. 6 shows saturation curves for input cDNA and a normalized cDNA normalized in accordance with the present invention using Nanopore cDNA sequencing.

To validate the present method, the inventors performed Nanopore cDNA sequencing on both the input cDNA library and a cDNA library generated by the present method. They compared the saturation curves for each of the libraries (FIG. 6). The curve for the present method is higher than the curve for the input cDNA by multiple factors. This indicates a more uniformly distributed cDNA library.

Applications of Selective Amplification

A primary application for the present method of selective amplification is for improving the discovery and detection of low abundance genes and isoforms. When combining the present method with sequencing, the sampling efficiency is increased for identifying all unique genes within a sample. This can be used for transcriptome annotation or for identifying novel genes and isoforms. Transcriptome annotation is primarily used for comparative biology efforts to understand the biology of different species. Novel gene and isoform discovery can help with identifying genes that are involved in biological mechanisms responsible for traits of interest. For instance, the present method can be used to help identify genes responsible for an organism's response to disease or even the genes involved in generating disease in the case of oncogenesis.

The present method can be applied to any double stranded cDNA library with known adapters on the ends and lengths that can be amplified via the PCR method. This means that it can be used in DNA sequencing. Another application for the present method is for increasing sampling efficiency during metagenomic sequencing to enhance the ability to identify low abundance micro-organisms within a sample. This could be used for understanding the microbiome and for identifying microorganisms that may be involved in disease or maintaining health.

A further application of the present method is for improved detection of genomic sequences from infectious diseases. This can either be used to amplify the genomic sequences of viruses, bacteria, or fungi in conjunction with a targeted method to improve overall limit of detection. This could also be used for mass screening where many samples are pooled prior to testing using either PCR or sequencing based methods.

Another important aspect of the present method is the ability to select cDNA having known lig sequences. This aspect could be applied for single cell sequencing where adapters are necessary for assigning reads to individual cells. In this application, cDNA sequences without cell identifying barcodes/adapters arise within the cDNA library. These are known as template switching oligo (TSO) artefacts and are undesirable in single cell sequencing projects due to not being assignable to a cell of origin. The present method can be applied with a short re-hybridization step to only select for cDNA sequences with the desired lig sequences thus effectively limiting the sequencing of TSO artefacts. The present method can also be performed with single cell cDNA libraries to both remove TSO artefacts and to improve transcriptome coverage per cell.

Discussion

The present method of selective cDNA amplification represents an innovative method of achieving greater non-targeted discovery/detection of low abundance nucleic acids.

It differs from existing normalization approaches by using an additive method where the current approaches use a depletion method. The additive method allows for the present method to be used with significantly smaller amounts of starting cDNA. The additive method also prevents over depletion and artificial chimerization, which is endemic to the DSNase method. The present method is also only length biased to the degree that PCR amplification is length biased. Thus it can be run successfully with longer cDNA molecules.

Accordingly, it can be seen that the present methods, adapters, compositions, dimers and kits have a wide range of commercial and academic applications. Some examples of these applications, each of which forms a further aspect of the present invention, are listed below:

RNA/DNA sequencing for discovering novel RNA.
RNA/DNA sequencing for the detection of low abundance RNA
RNA/DNA sequencing for detection of all RNA or DNA within a sample (including applications for single cell sequencing).
Metagenomic sequencing for discovering novel microbes
Metagenomic sequencing for detection of low abundance microbes
Metagenomic sequencing for detection of all expressed microbes within a sample
DNA library processing step to provide better signal to noise distinction with targeted approaches including qPCR and microarray assays.
For use in diagnostic pipelines where detection of DNA and RNA sequences is required (including cancer diagnostics for determining the presence of cancer and the type of cancer).
For use in RNA/DNA screening pipelines such as for quality control on gene editing to screen for issues with RNA production as a result of gene editing.
For use in treatment tracking to monitor the biological state in response to medical treatments.
For use in drug development to identify biomarkers that would help with designing or developing drugs (including vaccine development).
For use in screening samples for the presence of infectious diseases such as bacteria, viruses, and fungi.

The invention claimed is:

1. A method of selective amplification of single stranded cDNA, the method comprising:
   (i) providing a cDNA sample comprising double stranded cDNA templates, each template having a known 5' pre-attached adapter and a known 3' pre-attached adapter;
   (ii) denaturing the cDNA sample to produce single stranded cDNA templates;
   (iii) re-associating the cDNA sample to produce a mixture of post-association single stranded cDNA templates and post-association double stranded cDNA templates;
   (iv) annealing a 5' adapter complex to the 5' pre-attached adapter of at least one post-association single stranded cDNA template, and annealing a 3' adapter complex to the 3' pre-attached adapter of the same post-association single stranded cDNA template;
   (v) ligating an oligonucleotide from the 5' adapter complex to the 5' pre-attached adapter of the post-association single stranded cDNA template and ligating an oligonucleotide from the 3' adapter complex to the 3' pre-attached adapter of the same post-association single stranded cDNA template; and
   (vi) selectively amplifying the cDNA sample using primers specific to the ligated oligonucleotides, wherein:
   (A) the 5' adapter complex is a front oligonucleotide dimer comprising:
      (i) a front lig-oligonucleotide for ligating to the 5' pre-attached adapter of the post-association single stranded cDNA template; and
      (ii) a front link-oligonucleotide for annealing to the 5' pre-attached adapter and the front lig-oligonucleotide, the front link-oligonucleotide comprising a region complementary to the 5' pre-attached adapter and a region complementary to the front lig-oligonucleotide, such that, on annealing, an end of the front lig-oligonucleotide is adjacent an end of the 5' pre-attached adapter to enable ligation of the front lig-oligonucleotide to the 5' pre-attached adapter at a ligation site; and (B) the 3' adapter complex is a back oligonucleotide dimer comprising:
  (i) a back lig-oligonucleotide for ligating to the 3' pre-attached adapter of the post-association single stranded cDNA template; and
  (ii) a back link-oligonucleotide for annealing to the 3' pre-attached adapter and the back lig-oligonucleotide, the back link-oligonucleotide comprising a region complementary to the 3' pre-attached adapter and a region complementary to the back lig-oligonucleotide, such that, on annealing, an end of the back lig-oligonucleotide is adjacent an end of the 3' pre-attached adapter to enable ligation of the back lig-oligonucleotide to the 3' pre-attached adapter at a ligation site; and wherein:

(C) the front link-oligonucleotide comprises:
  (i) a template overhang region at an end of the front link-oligonucleotide proximal the region complementary to the 5' pre-attached adapter, the template overhang region being non-complementary to a corresponding region of the post-association single stranded cDNA template; and/or
  (ii) a lig-oligonucleotide overhang region at an end of the front link-oligonucleotide proximal the region complementary to the front lig-oligonucleotide, the lig-oligonucleotide overhang region being non-complementary to a corresponding region of the front lig-oligonucleotide; and/or (D) the back link-oligonucleotide comprises:
  (i) a template overhang region at an end of the back link-oligonucleotide proximal the region complementary to the 3' pre-attached adapter, the template overhang region being non-complementary to a corresponding region of the post-association single stranded cDNA template; and/or
  (ii) a lig-oligonucleotide overhang region at an end of the back link-oligonucleotide proximal the region complementary to the back lig-oligonucleotide, the lig-oligonucleotide overhang region being non-complementary to a corresponding region of the back lig-oligonucleotide.

2. A method as claimed in claim 1 wherein the template overhang region and/or lig-oligonucleotide overhang region is between 1 bp and 20 bp in length.

3. A method as claimed in claim 1 wherein the front and/or back link-oligonucleotide has a length of less than 200 nt.

4. A method as claimed in claim 1 wherein the front link-oligonucleotide and/or the back link-oligonucleotide provides at least 5 bp of complementary binding either side of the ligation site.

5. A method as claimed in claim 1 wherein a nucleotide sequence of the front oligonucleotide dimer is different and non-complementary to a nucleotide sequence of the back oligonucleotide dimer.

6. A method as claimed in claim 1 wherein at least one of the front oligonucleotide dimer and the back oligonucleotide dimer is annealable to the post-association single stranded cDNA template at a temperature of over 30° C.

7. A method as claimed in claim 1 wherein a concentration of the front oligonucleotide dimer and/or a concentration of the back oligonucleotide dimer exceeds a concentration of a predicted total single stranded cDNA concentration in the cDNA sample.

8. Use of a method as claimed in claim 1 in a process of RNA or DNA sequencing.

9. Use of a method as claimed in claim 1 in a process of metagenomic sequencing for discovery of new microbes and/or detection of microbes.

10. Use of a method as claimed in claim 1 in a process of screening DNA or RNA samples, or screening genetic samples for the presence of infectious diseases.

11. Use of a method as claimed in claim 1 in a process of detecting a nucleic acid biomarker.

12. A method of selective amplification of cDNA comprising known adapter sequences, the method comprising:
  (i) providing a cDNA sample comprising double stranded cDNA templates, a portion of the templates having a known 5' pre-attached adapter and a known 3' pre-attached adapter;
  (ii) denaturing the cDNA sample to produce single stranded cDNA templates;
  (iii) annealing a 5' adapter complex to the 5' pre-attached adapter of at least one single stranded cDNA template, and annealing a 3' adapter complex to the 3' pre-attached adapter of the same single stranded cDNA template;
  (iv) ligating an oligonucleotide from the 5' adapter complex to the 5' pre-attached adapter of the single stranded cDNA template and ligating an oligonucleotide from the 3' adapter complex to the 3' pre-attached adapter of the same single stranded cDNA template; and
  (v) selectively amplifying the cDNA sample using primers specific to the ligated oligonucleotides, wherein:

(A) the 5' adapter complex is a front oligonucleotide dimer comprising:
  (i) a front lig-oligonucleotide for ligating to the 5' pre-attached adapter of the single stranded cDNA template; and
  (ii) a front link-oligonucleotide for annealing to the 5' pre-attached adapter and the front lig-oligonucleotide, the front link-oligonucleotide comprising a region complementary to the 5' pre-attached adapter and a region complementary to the front lig-oligonucleotide, such that, on annealing, an end of the front lig-oligonucleotide is adjacent an end of the 5' pre-attached adapter to enable ligation of the front lig-oligonucleotide to the 5' pre-attached adapter at a ligation site; and (B) the 3' adapter complex is a back oligonucleotide dimer comprising:
  (i) a back lig-oligonucleotide for ligating to the 3' pre-attached adapter of the single stranded cDNA template; and
  (ii) a back link-oligonucleotide for annealing to the 3' pre-attached adapter and the back lig-oligonucleotide, the back link-oligonucleotide comprising a region complementary to the 3' pre-attached adapter and a region complementary to the back lig-oligonucleotide, such that, on annealing, an end of the back lig-oligonucleotide is adjacent an end of the 3' pre-attached adapter to enable ligation of the back lig-oligonucleotide to the 3' pre-attached adapter at a ligation site; and wherein:

(C) the front link-oligonucleotide comprises:
  (i) a template overhang region at an end of the front link-oligonucleotide proximal the region complementary to the 5' pre-attached adapter, the template overhang region being non-complementary to a corresponding region of the single stranded cDNA template; and/or
  (ii) a lig-oligonucleotide overhang region at an end of the front link-oligonucleotide proximal the region complementary to the front lig-oligonucleotide, the lig-oligonucleotide overhang region being non-complementary to a corresponding region of the front lig-oligonucleotide; and/or
(D) the back link-oligonucleotide comprises:
  (i) a template overhang region at an end of the back link-oligonucleotide proximal the region complementary to the 3' pre-attached adapter, the template overhang region being non-complementary to a corresponding region of the single stranded cDNA template; and/or
  (ii) a lig-oligonucleotide overhang region at an end of the back link-oligonucleotide proximal the region complementary to the back lig-oligonucleotide, the lig-oligonucleotide overhang region being non-complementary to a corresponding region of the back lig-oligonucleotide.

13. An oligonucleotide dimer composition for use in a method according to claim 1 for selective amplification of single stranded cDNA by ligation of an oligonucleotide to a 5' and a 3' end of a post-association single stranded cDNA template having known 5' and 3' pre-attached adapters, wherein the composition comprises:
(A) a front oligonucleotide dimer comprising:
  (i) a front lig-oligonucleotide for ligating to the 5' pre-attached adapter of the post-association single stranded cDNA template; and
  (ii) a front link-oligonucleotide for annealing to the 5' pre-attached adapter and the front lig-oligonucleotide, the front link-oligonucleotide comprising a region complementary to the 5' pre-attached adapter and a region complementary to the front lig-oligonucleotide,
  such that, on annealing, an end of the front lig-oligonucleotide is adjacent an end of the 5' pre-attached adapter to enable ligation of the front lig-oligonucleotide to the 5' pre-attached adapter at a ligation site; and
(B) a back oligonucleotide dimer comprising:
  (i) a back lig-oligonucleotide for ligating to the 3' pre-attached adapter of the post-association single stranded cDNA template; and
  (ii) a back link-oligonucleotide for annealing to the 3' pre-attached adapter and the back lig-oligonucleotide, the back link oligonucleotide comprising a region complementary to the 3' pre-attached adapter and a region complementary to the back lig-oligonucleotide,
  such that, on annealing, an end of the back lig-oligonucleotide is adjacent an end of the 3' pre-attached adapter to enable ligation of the back lig-oligonucleotide to the 3' pre-attached adapter at a ligation site,
wherein:
(C) the front link-oligonucleotide comprises:
  (i) a template overhang region at an end of the front link-oligonucleotide proximal the region complementary to the 5' pre-attached adapter, the template overhang region being non-complementary to a corresponding region of the post-association single stranded cDNA template; and/or
  (ii) a lig-oligonucleotide overhang region at an end of the front link-oligonucleotide proximal the region complementary to the front lig-oligonucleotide, the lig-oligonucleotide overhang region being non-complementary to a corresponding region of the front lig-oligonucleotide; and/or
(D) the back link-oligonucleotide comprises:
  (i) a template overhang region at an end of the back link-oligonucleotide proximal the region complementary to the 3' pre-attached adapter, the template overhang region being non-complementary to a corresponding region of the post-association single stranded cDNA template; and/or
  (ii) a lig-oligonucleotide overhang region at an end of the back link-oligonucleotide proximal the region complementary to the back lig-oligonucleotide, the lig-oligonucleotide overhang region being non-complementary to a corresponding region of the back lig-oligonucleotide.

14. An oligonucleotide dimer composition as claimed in claim 13 wherein the template overhang region and/or lig-oligonucleotide overhang region is between 1 bp and 20 bp in length.

15. An oligonucleotide dimer composition as claimed in claim 13 wherein the front and/or back link-oligonucleotide has a length of less than 200 nt.

16. An oligonucleotide dimer composition as claimed in claim 13 wherein, in use of the composition, the front link-oligonucleotide and/or the back link-oligonucleotide provides at least 5 bp of complementary binding either side of the ligation site.

17. An oligonucleotide dimer composition as claimed in claim 13 wherein a nucleotide sequence of the front oligonucleotide dimer is different and non-complementary to a nucleotide sequence of the back oligonucleotide dimer.

18. An oligonucleotide dimer composition as claimed in claim 13 wherein the front oligonucleotide dimer and/or the back oligonucleotide dimer is annealable to the post-association single stranded cDNA template at a temperature of over 30° C.

19. A selective amplification kit for selective amplification of cDNA comprising known adapter sequences from a cDNA sample, the cDNA sample comprising cDNA templates having known 5' and 3' pre-attached adapters, the kit comprising means for preparing an oligonucleotide dimer composition according to claim 11 and means for implementing the method of selective amplification as claimed in claim 2,
  wherein the means for preparing an oligonucleotide dimer composition comprise:
  (i) a front lig-oligonucleotide for ligating to the 5' pre-attached adapter;
  (ii) a front link-oligonucleotide for annealing to the 5' pre-attached adapter and the front lig-oligonucleotide, the front link-oligonucleotide comprising a region complementary to the 5' pre-attached adapter and a region complementary to the front lig-oligonucleotide,
  such that, on annealing, an end of the front lig-oligonucleotide is adjacent an end of the 5' pre-attached adapter to enable ligation of the front lig-oligonucleotide to the 5' pre-attached adapter at a ligation site;
  (iii) a back lig-oligonucleotide for ligating to the 3' pre-attached adapter; and (iv) a back link-oligonucleotide for annealing to the 3' pre-attached adapter and the back lig-oligonucleotide, the back link oligonucleotide comprising a region complementary to the 3' pre-attached adapter and a region complementary to the back lig-oligonucleotide, such that, on annealing, an end of the back lig-oligonucleotide is adjacent an end of the 3' pre-attached adapter to enable ligation of the back lig-oligonucleotide to the 3' pre-attached adapter at a ligation site, wherein:

the front link-oligonucleotide comprises:
(i) a template overhang region at an end of the front link-oligonucleotide proximal the region complementary to the 5' pre-attached adapter, the template overhang region being non-complementary to a corresponding region of the cDNA template; and/or
(ii) a lig-oligonucleotide overhang region at an end of the front link-oligonucleotide proximal the region complementary to the front lig-oligonucleotide, the lig-oligonucleotide overhang region being non-complementary to a corresponding region of the front lig-oligonucleotide; and/or the back link-oligonucleotide comprises:
(i) a template overhang region at an end of the back link-oligonucleotide proximal the region complementary to the 3' pre-attached adapter, the template overhang region being non-complementary to a corresponding region of the cDNA template; and/or
(ii) a lig-oligonucleotide overhang region at an end of the back link-oligonucleotide proximal the region complementary to the back lig-oligonucleotide, the lig-oligonucleotide overhang region being non-complementary to a corresponding region of the back lig-oligonucleotide.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
ggcaatgaag tcgcagggtt g                                            21

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
aagcagtggt atcaacgcag ag                                           22

<210> SEQ ID NO 3
<211> LENGTH: 40
<212> TYPE: DNA
<213> ORGANISM: Artificial Sequence
<220> FEATURE:
<223> OTHER INFORMATION: oligonucleotide

<400> SEQUENCE: 3
atagcgttga taccactgct tctcacgaca gactcgctaa                        40

<210> SEQ ID NO 4
<211> LENGTH: 25
<212> TYPE: DNA
<213> ORGANISM: Artificial Sequence
<220> FEATURE:
<223> OTHER INFORMATION: oligonucleotide
```

```
<400> SEQUENCE: 4
tggactgatg cgagtctgtc gtgag                                         25

<210> SEQ ID NO 5
<211> LENGTH: 38
<212> TYPE: DNA
<213> ORGANISM: Artificial Sequence
<220> FEATURE:
<223> OTHER INFORMATION: oligonucleotide

<400> SEQUENCE: 5
aatgacgctg gacgaacacg gcaatgaagt cgcagaca                           38

<210> SEQ ID NO 6
<211> LENGTH: 27
<212> TYPE: DNA
<213> ORGANISM: Artificial Sequence
<220> FEATURE:
<223> OTHER INFORMATION: oligonucleotide

<400> SEQUENCE: 6
gtgttcgtcc agcgtccagg tgagtgg                                       27

<210> SEQ ID NO 7
<211> LENGTH: 27
<212> TYPE: DNA
<213> ORGANISM: Artificial Sequence
<220> FEATURE:
<223> OTHER INFORMATION: primer

<400> SEQUENCE: 7
ccactcacct ggacgctgga cgaacac                                       27

<210> SEQ ID NO 8
<211> LENGTH: 59
<212> TYPE: DNA
<213> ORGANISM: Artificial Sequence
<220> FEATURE:
<223> OTHER INFORMATION: template
<220> FEATURE:
<221> NAME/KEY: misc_feature
<222> LOCATION: (23)..(38)
<223> OTHER INFORMATION: n is a, c, t or g

<400> SEQUENCE: 8
aagcagtggt atcaacgcag agnnnnnnnn nnnnnnnnca accctgcgac ttcattgcc    59
```